US00PP26523P3

(12) United States Plant Patent
Lyrene

(10) Patent No.: US PP26,523 P3
(45) Date of Patent: Mar. 22, 2016

(54) BLUEBERRY PLANT NAMED 'FL98-325'

(50) Latin Name: ***Vaccinium corymbosum* L.**
Varietal Denomination: FL98-325

(71) Applicant: Florida Foundation Seed Producers, Inc., Marianna, FL (US)

(72) Inventor: Paul M. Lyrene, Micanopy, FL (US)

(73) Assignee: Florida Foundation Seed Producers, Inc., Marianna, FL (US)

( * ) Notice: Subject to any disclaimer, the term of this patent is extended or adjusted under 35 U.S.C. 154(b) by 205 days.

(21) Appl. No.: 13/998,282

(22) Filed: Oct. 16, 2013

(65) Prior Publication Data

US 2015/0106980 P1 Apr. 16, 2015

(51) Int. Cl.
*A01H 5/08* (2006.01)

(52) U.S. Cl.
USPC ..... Plt./157
CPC ..... *A01H 5/08* (2013.01)

(58) Field of Classification Search
USPC ..... Plt./157
See application file for complete search history.

(56) References Cited

U.S. PATENT DOCUMENTS

PP12,165 P2 10/2001 Lyrene
PP12,783 P2 7/2002 Lyrene
PP20,818 P3 * 3/2010 Ilamo et al. ..... Plt./157

OTHER PUBLICATIONS

HortScience vol. 45(5) May 2010. Register of New Fruit and Nut Cultivars List 45 retrieved on Jul. 1, 2015, retrieved from the Internet at <http://hortsci.ashspublications.org/content/45/5/716.short> pp. 716, 721-723.*

Australian Government IP Australia Plant Varieties Journal Quarter One 2012 vol. 25, No. 1, retrieved on Jul. 1, 2015, retrieved from the internet at <http://www.ipaustralia.gov.au/pdfs/pbr/PVJ_Vol_25_1_supplement.pdf> pp. 1, 292-298.*

* cited by examiner

*Primary Examiner* — June Hwu
(74) *Attorney, Agent, or Firm* — Dentons US LLP

(57) ABSTRACT

FL98-325 is a new and distinct southern highbush blueberry (*Vaccinium corymbosum* L.) variety distinguished by a low chilling requirement, upright growth habit, and fruit that are extremely firm, sweet, with a small dry picking scar.

6 Drawing Sheets

Latin name of the genus and species of the plant claimed: *Vaccinium corymbosum* L.

Variety denomination: 'FL98-325'.

BACKGROUND OF THE INVENTION

The present invention relates to a new and distinct hybrid variety of southern highbush blueberry (*Vaccinium corymbosum* L.) named 'FL98-325'. 'FL98-325' is a blueberry clone distinguished by its low chilling requirement, vigorous, upright bush, and large, sweet, extremely firm berries that ripen from mid-April through early May when grown in North Florida. Several thousand plants of 'FL98-325' have been propagated by softwood stem cuttings in Gainesville, Fla., and the resulting plants have all been phenotypically indistinguishable from the original plant. Contrast is made to 'Emerald' (U.S. Plant Pat. No. 12,165), an important variety widely planted in the southeastern United States. The claimed plant is important because it is more upright and has earlier maturing fruit than 'Emerald'. Fruit of 'FL98-325' are also sweeter and have an extremely firm texture with a small dry picking scar. 'FL98-325' fruit can be mechanically harvested with less damage than 'Emerald' berries.

'FL98-325' originated as a seedling from a cross between 'FL96-27' (unpatented) as the female (seed) parent and 'Windsor' (U.S. Plant Pat. No. 12,783) as the male (pollen) parent. This cross was made as part of the University of Florida breeding program in a greenhouse at Gainesville, Fla., in February 1996. The seedling was planted in a high-density field nursery in May 1997 and the first fruit were evaluated in April 1998. After the second year of fruiting in the field, in the spring of 1999, 'FL98-325' was propagated by softwood stem cuttings, and an experimental 20-plant test plot was established as part of a variety test at Windsor, Fla., in January 2000. Based on the growth, yield, and fruit quality of this plot, 'FL98-325' was repropagated by softwood stem cuttings and an additional 50-plant experimental plot was planted in Windsor, Fla., in January 2002. Experimental test plots ranging from 50 to 500 plants were established in Archer, Haines City, and Waldo, Fla. These plots have been observed during flowering and ripening each year, and no mutations or off-type plants have been observed.

'FL98-325' differs from the proprietary parent 'FL96-27' (unpatented) in that 'FL98-325' has firmer fruit and a lower chilling requirement. Additionally, 'FL98-325' differs from the parent 'Windsor' (U.S. Plant Pat. No. 12,783) in that 'FL98-325' has firmer fruit, a smaller picking scar, and a more upright growth habit. 'FL98-325' differs from the commercial variety 'Emerald' (U.S. Plant Pat. No. 12,165), an important variety widely planted in the southeastern United States, in that 'FL98-325' has a more upright growth habit, and a more elongated, lanceolate leaf shape compared to the obovate shape of 'Emerald' leaves. 'FL98-325' berries are darker-colored, firmer, and have a sweeter, low-acid flavor than 'Emerald' berries.

SUMMARY OF THE INVENTION

Blueberry variety 'FL98-325' exhibits outstanding and distinguishing characteristics when grown under normal horticultural practices in Florida, including: (1) a low chilling requirement, particularly for the flower buds; (2) a vigorous, upright bush; (3) early ripening (50% ripe berries in North Florida around April 20); and (4) large, sweet, extremely firm berries with a small, dry picking scar and good post-harvest keeping quality.

BRIEF DESCRIPTION OF THE DRAWINGS

The accompanying photographs, taken of a 4-year-old plant, show typical bush, flower, and fruit characteristics for 'FL98-325'. Colors shown are as true as can be reasonably reproduced by photographic procedures and may differ from those cited in the detailed description, which accurately describes the colors of 'FL98-325'.

DETAILED BOTANICAL DESCRIPTION

Figure 1:
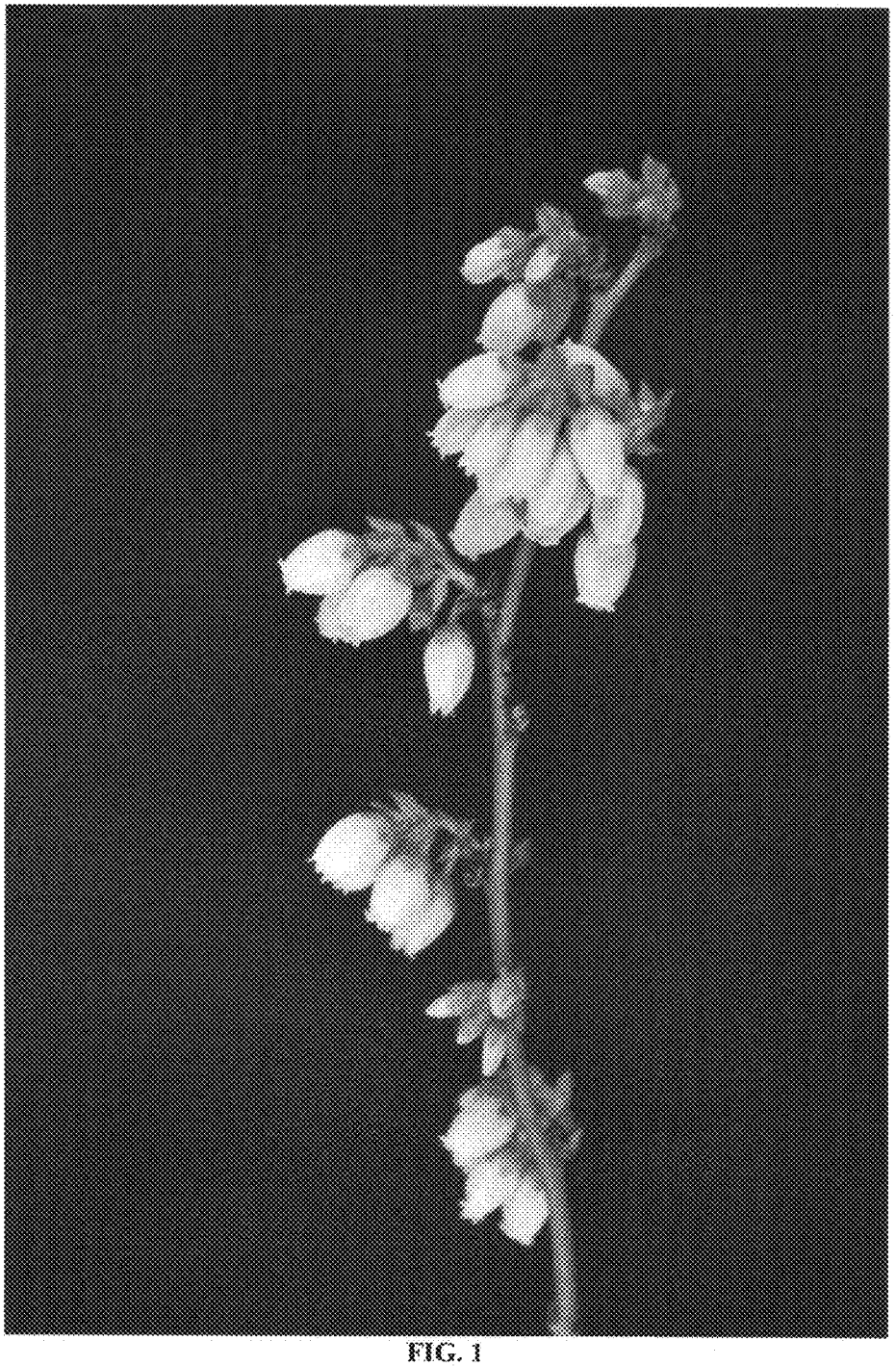
FIG. 1—Shows several clusters of opening 'FL98-325' flowers during the early stages of flowering in February.
Figure 2:
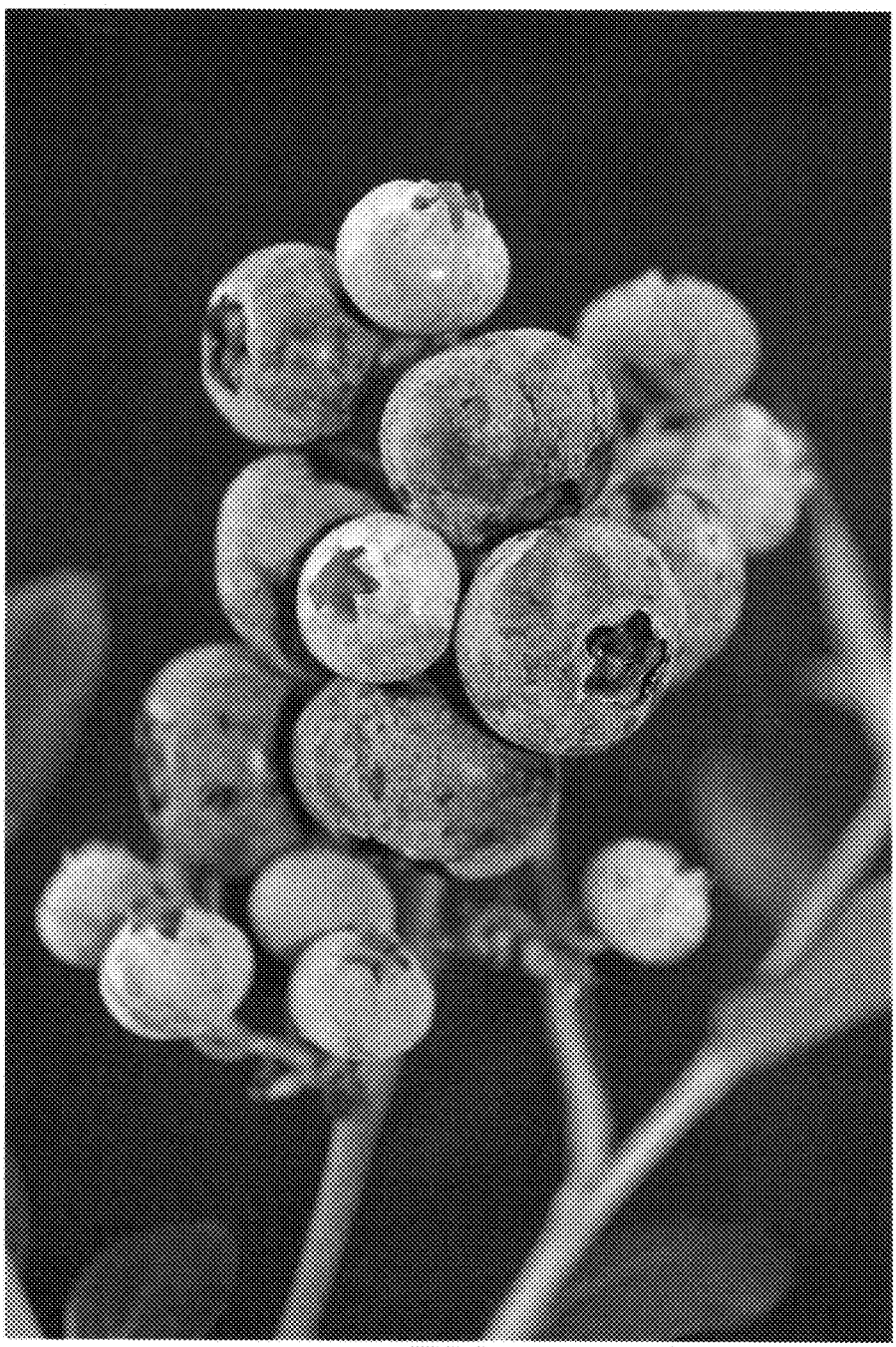
FIG. 2—Shows a typical cluster of 'FL98-325' berries during the fruit ripening season.
Figure 3:
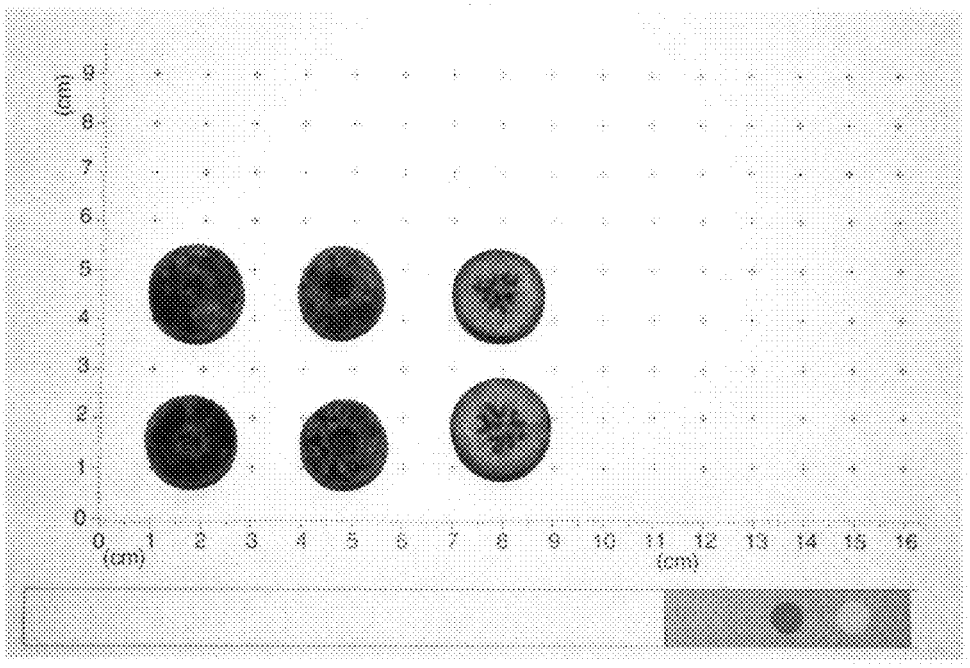
FIG. 3—Shows a close-up of 'FL98-325' berries with a scale bar. The berries are normally much lighter in color than indicated in FIG. 3, in which the surface wax has been rubbed off by handling during harvest and transport.
Figure 4:
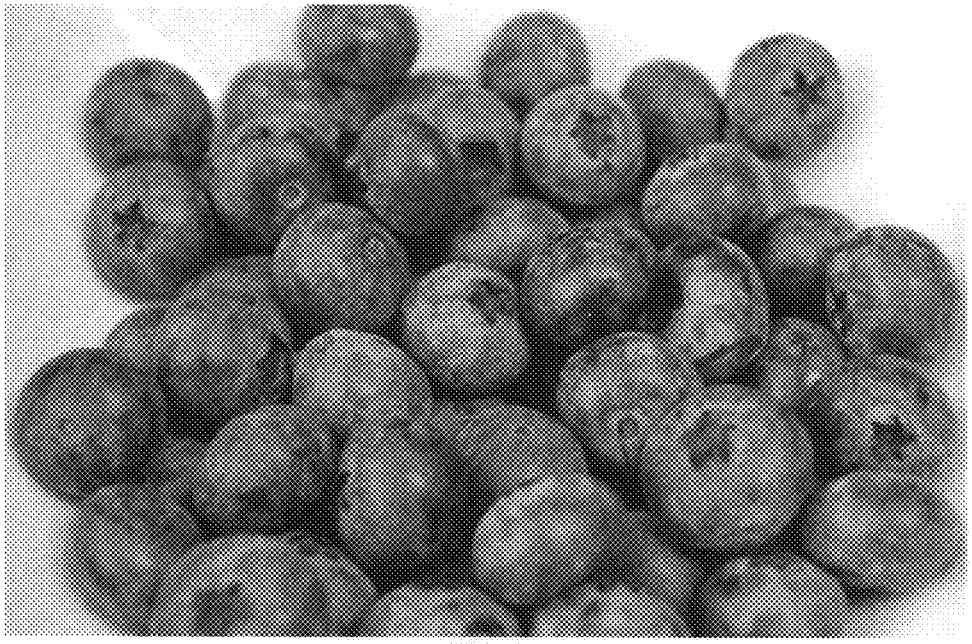
FIG. 4—Shows a close-up of harvested 'FL98-325' berries.
Figure 5:
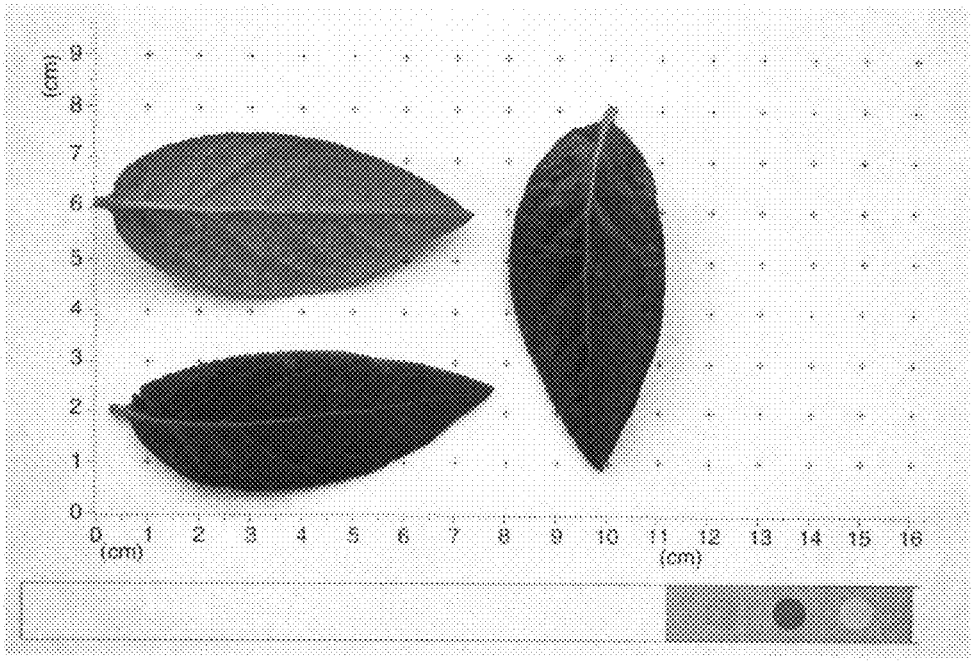
FIG. 5—Shows a close-up of mature 'FL98-325' leaves with a scale bar.
Figure 6:
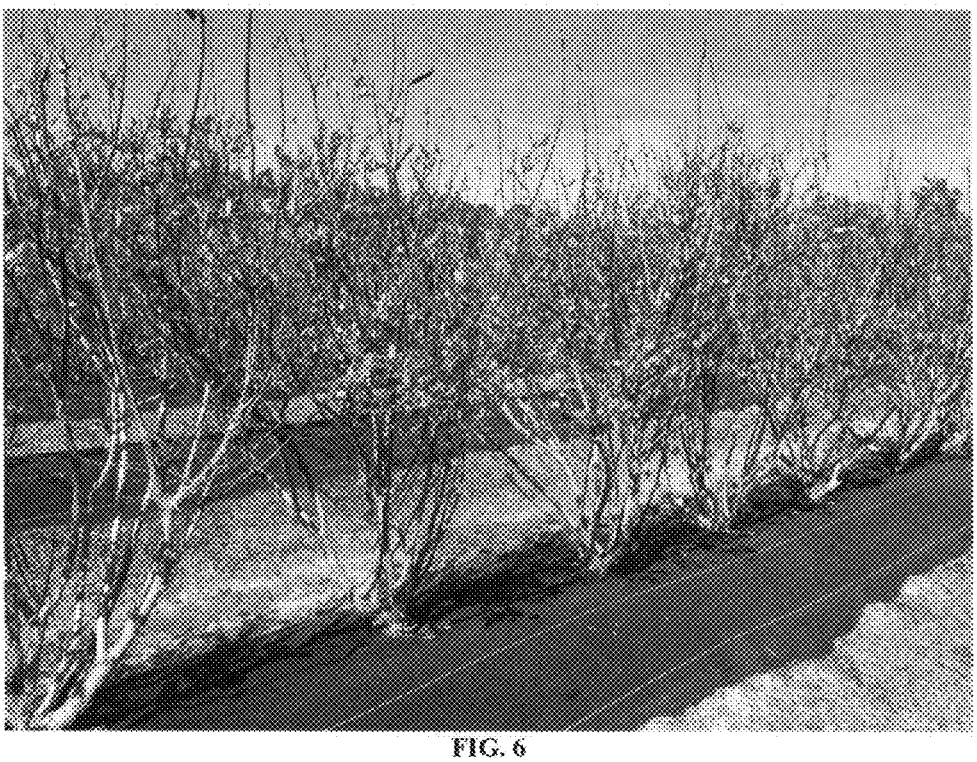
FIG. 6—Shows a group of three-year-old 'FL98-325' plants in January with the upright plant architecture visible.

The following detailed description sets forth the distinctive characteristics of 'FL98-325'. The data that define these characteristics were collected from asexual reproductions carried out in Florida. The plant history was taken on a plot of 500 three-year-old plants growing in a commercial field near Windsor, Fla. Certain characteristics may vary with plant age. 'FL98-325' has not been observed under all possible environmental conditions, and the measurements given may vary when grown in different environments. Where means are given, the sample size was 20. Color descriptions are based on The Royal Horticultural Society (R.H.S.) Colour Chart by The Royal Horticultural Society, London, Fifth Edition, 2007. When the RHS color designations differ from the accompanying photographs, the R.H.S. color designations are accurate.

Phenotypic Description of *Vaccinium corymbosum* L. ('FL98-325')

Plant:

- *Plant height*.—Mean of 2.0 m.
- *Canopy* (*diameter measured at widest part of the bush*).—Mean of 1.5 m.
- *Plant vigor*.—Medium. Vigor is less than 'Emerald' (U.S. Plant Pat. No. 12,165) and 'Windsor' (U.S. Plant Pat. No. 12,783).
- *Growth habit*.—Upright.
- *Flower bud density* (*number*) *along flowering twigs in January*.—Medium to high.
- *Twigginess*.—Medium.
- *Tendency toward evergreenness*.—Low to medium.
- *Productivity*.—In northeast Florida, 'FL98-325' produces 2 to 3 kg per season from plants 3 years or older.
- *Chilling requirement*.—Based on the evaluation locations, the chilling requirement is expected to be approximately 300 hours below 7° C. When evaluated in trial sites receiving an average less than 300 hours below 7° C., 'FL98-325' has performed poorly.
- *Cold hardiness*.—'FL98-325' has not been grown in temperate climates with extremely cold winter temperatures. Plants have survived winter freezes of −8° C. with minimal damage.
- *Ease of propagation*.—'FL98-325' has only been propagated from softwood stem cuttings, where the rooting percentage has often been low.

Trunk and branches:

- *Suckering tendency*.—Low. Three-year-old plants typically have 5 to 7 major canes arising from a crown 30 cm in diameter.
- *Surface texture* (*of strong, 6-month-old shoots observed in August*).—Smooth.
- *Surface texture* (*of 3-year-old and older wood*).—Rough.
- *Color of new twigs observed in August in the field*.—Yellow-green 144C.
- *Color of 3-year-old, rough-textured canes*.—Greyed green 197D.
- *Internode length* (*strong, upright shoots measured in February*).—Mean of 15.5 mm.

Leaves:

- *Length* (*including petiole, from tip of petiole to end of blade*).—Mean of 8.9 cm.
- *Width* (*at widest point*).—Mean of 3.9 cm.
- *Shape*.—Ovate to lanceolate, with an acute base and acuminate apex.
- *Margin*.—Entire. Very slight undulation of margin toward petiole end of leaf.
- *Color*.—Upper surface: Green 139A. Lower surface: Yellow-green 147B.
- *Pubescence*.—Upper surface of leaves: Absent. Lower surface of leaves: Absent. Margins: Absent.
- *Timing of vegetative bud burst*.—Medium.
- *Relative time of leafing versus flowering*.—When not treated with hydrogen cyanamide in mid-winter, leafing is delayed relative to flowering.

Flowers:

- *Arrangement*.—Flowers are arranged alternately along a short, leafless, deciduous branch.
- *Fragrance*.—Slight rose fragrance.
- *Shape*.—Cylindrical to urceolate.
- *Flowering period*.—Mean date of 50% open flowers in Windsor, Fla. is February 13; averages one week later than 'Emerald'.
- *Cluster* (*tight, medium, loose*).—Loose.
- *Number of flowers per cluster*.—Mean of 4.9.
- *Pedicel*.—Length at time of anthesis: Mean of 6.3 mm. Color at time of anthesis: Green 144C with Red 46A on sun-exposed side.
- *Peduncle*.—Length at time of anthesis: Highly variable, mean of 11.2 mm. Color at time of anthesis: Yellow-green 150B with Red-purple 60A on sun-exposed side.
- *Calyx*.—Surface texture: Smooth. Diameter: Mean of 5.8 mm. Color: Green 143A.
- *Corolla*.—Diameter: Mean of 7.2 mm. Length (from pedicel attachment point to corolla tip excluding the pedicel): Mean of 11.5 mm. Aperture diameter: Mean of 5.0 mm. Texture: Smooth. Color: Off-white NN155A.

Reproductive organs:

*Style*.—Length (top of ovary to stigma tip): Mean of 9.0 mm. Color: Yellow-green 150C.

*Location of tip of stigma relative to lip of the corolla*.—Stigma tip is approximately 1 mm below the corolla lip.

*Anthers*.—Color: Greyed-orange 163A.

*Pollen*.—Abundance of shed: High. Staining with 2% acetocarmine (a measure of potential pollen fertility): 94%. Pollen germination: 98%. Color: Greyed-yellow 162B.

*Self-fruitfulness*.—Low to medium. Planting in field configurations that promote cross fertilization with other southern highbush varieties is recommended for all southern highbush blueberry plants grown in Florida.

Fruit:

*Mean date of first commercial harvest* (*25% of berries ripe*).—April 15.

*Mean date of mid-harvest*.—April 25.

*Mean date of last harvest*.—May 5.

*Diameter of calyx aperture on mature berry*.—Mean of 6.8 mm.

*Size and shape of calyx lobes on mature berry*.—Very small lobes, semi-erect, straight with slight incurving. Medium calyx basin.

*Pedicel length on ripe berry*.—Mean of 6.5 mm.

*Detachment force for ripe berries* (*easy, medium, hard*).—Easy.

*Fruit cluster density*.—Sparse.

*Number of berries per cluster*.—Mean of 4.1.

*Fruiting type*.—On one-year-old and current season's shoots.

Berry:

*Cluster* (*tight, medium, loose*).—Medium to loose.

*Weight* (*on well-pruned plants*).—Mean of 2.6 g.

*Height*.—Mean of 12.9 mm.

*Width*.—Mean of 18.4 mm.

*Shape*.—Round to oblate.

*Surface color of mature berries while on the plant*.—Violet-blue 97B.

*Surface color of ripe berry after polishing*.—Black 203C.

*Immature berry color, with bloom*.—Greyed-green 191B.

*Immature berry color without bloom*.—Yellow-green 146B.

*Surface wax*.—Low amount of surface wax makes the berry appear darker. The surface wax on 'FL98-325' has only medium resistance to abrasion.

*Pedicel scar*.—Small and dry. Mean of 1.8 mm.

*Firmness*.—Extremely firm.

*Flavor*.—Sweet, very low acid, mild flavor.

*Texture*.—Very good, crisp texture, juicy, small seeds, and no stone cells present.

Seeds:

*Color of dried seeds*.—Greyed-orange N167A.

*Weight of well-developed dried seed*.—Mean of 0.5 mg.

*Length of well-developed dried seed*.—Mean of 1.8 mm.

Use: 'FL98-325' produces southern highbush blueberries suitable for both the fresh and processed fruit markets.

Resistance to diseases, insects, and mites: 'FL98-325' has grown vigorously and shows medium to good bush survival in the field. It appears to have only average resistance to stem blight (*Botryosphaeria* spp.) and root rot (*Phytophthora cinnamoni*), with some young plants dying soon after planting. Susceptibility to stem blight is greater than 'Emerald' and 'Windsor'. The reaction of 'FL98-325' to the fungal species that cause summer leaf spots is typical of other southern highbush varieties, and fungicide applications may be needed after harvest to reduce foliar diseases. No unusual susceptibility to insects or mites has been observed.

What is claimed is:

1. A new and distinct variety of southern highbush blueberry plant named 'FL98-325', as illustrated and described herein.

* * * * *